(12) United States Patent
Haque et al.

(10) Patent No.: US 6,289,729 B1
(45) Date of Patent: Sep. 18, 2001

(54) ULTRASONIC SENSOR FOR WEB-GUIDING APPARATUS

(75) Inventors: Md M. Haque, Edmond; Darcy Winter, Oklahoma City; Dale Hueppelsheuser, Jones; John P. Newton, Edmond; Greg A. Storie, Midwest City, all of OK (US)

(73) Assignee: Fife Corporation, Oklahoma City, OK (US)

( * ) Notice: Subject to any disclaimer, the term of this patent is extended or adjusted under 35 U.S.C. 154(b) by 0 days.

(21) Appl. No.: 09/221,039

(22) Filed: Dec. 28, 1998

(51) Int. Cl.⁷ ................................................. G01N 29/20
(52) U.S. Cl. .............................................. 73/159; 73/599
(58) Field of Search ............................... 73/599, 609, 610, 73/611, 612, 597, 602, 159; 226/15, 18, 19, 21; 367/118; 340/675, 676

(56) References Cited

U.S. PATENT DOCUMENTS

| | | |
|---|---|---|
| 3,225,988 | 12/1965 | Drenning . |
| 3,342,284 | 9/1967 | Baird . |
| 3,570,624 | 3/1971 | Denville ................................. 181/0.5 |
| 4,291,577 | 9/1981 | Baum et al. ............................ 73/597 |
| 4,441,367 | 4/1984 | Daws et al. ............................ 73/597 |
| 4,493,065 | * 1/1985 | Sword, Jr. ............................... 367/96 |
| 4,519,249 | 5/1985 | Hunt ...................................... 73/596 |
| 4,730,492 | 3/1988 | Burk ...................................... 73/597 |
| 4,789,431 | 12/1988 | Typpo .................................. 162/263 |
| 4,833,928 | 5/1989 | Luukkala et al. ................... 73/862.39 |
| 4,901,292 | 2/1990 | Schrauwen . |
| 5,021,674 | 6/1991 | Brunner ................................ 250/561 |
| 5,058,793 | 10/1991 | Neville et al. ........................ 226/15 |
| 5,072,414 | 12/1991 | Buisker et al. ...................... 364/550 |
| 5,126,946 | 6/1992 | Ko ........................................ 364/469 |
| 5,161,126 | * 11/1992 | Marcus ................................. 367/99 |
| 5,565,627 | * 10/1996 | Dorr ...................................... 73/599 |
| 5,583,828 | * 12/1996 | Arai et al. ............................ 73/159 |
| 5,803,334 | * 9/1998 | Patel et al. ........................... 226/45 |
| 5,834,877 | * 11/1998 | Buisker et al. ...................... 310/322 |

FOREIGN PATENT DOCUMENTS

| | | |
|---|---|---|
| 3900928 | 6/1990 | (DE) . |
| 4209546 | 9/1993 | (DE) . |
| 0201576 | 9/1985 | (EP) . |

* cited by examiner

*Primary Examiner*—Helen Kwok
(74) *Attorney, Agent, or Firm*—Dunlap, Codding & Rogers P.C.

(57) ABSTRACT

A sensor system for determining the position of at least one edge of a web of material is provided. The sensor system includes a transmitter and a receiver disposed on opposite sides of the web. The transmitter is capable of selectively transmitting ultrasonic signals, and the receiver is capable of receiving such ultrasonic signals and generating output signals indicative of the position of the web. The sensor system further includes a sensor drive circuit adapted to periodically transmit to the transmitter a transmitter drive signal representative of substantially one cycle of a signal, and to receive signals from the receiver with each signal being indicative of the position of the web.

31 Claims, 3 Drawing Sheets

ULTRASONIC SENSOR FOR WEB-GUIDING APPARATUS

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Ultrasonic sensors having a transmitter disposed on one side of a web and a receiver disposed on the other side of the web for locating the position of an edge of the web therebetween, are known in the art. Such ultrasonic sensors are mounted perpendicular to the web direction of travel and suffer from problems due to the reflection of sound between the transmitter, the web, and the receiver. Noise is thereby introduced into the signal produced by the receiver, and reduces the accuracy of the prior art ultrasonic sensors.

Previously, people in the art attempted to solve this problem by changing the angle of the ultrasonic sensor with respect to the web (away from the perpendicular orientation discussed above), as well as designing sensor housing to maintain non-parallelism between transmit and receive sides, so that the sound reflections would be reflected away from the receiver. Although the prior art method reduced the problem of sound reflection somewhat, it is less desirable to have the prior art ultrasonic sensor mounted angularly with respect to the direction of web travel. In addition, this angular mounting limits the effective sensing gap and allows less web plane change than that of perpendicular mounting.

Thus, there is a need for an ultrasonic sensor which does not suffer from the aforementioned problems caused by the reflection of the sound waves as described hereinabove. It is to such an improved ultrasonic sensor that the present invention is directed.

SUMMARY OF THE INVENTION

The present invention relates to a sensor system for determining the position of at least one edge of a web of material. Broadly, the sensor system comprises a transmitter, a receiver, and a sensor drive circuit.

The transmitter is capable of selectively transmitting ultrasonic signals. The receiver is positioned to receive at least a portion of the ultrasonic signals transmitted by the transmitter. In response thereto, the receiver generates receiver output signals indicative of the position of the web.

The sensor drive circuit periodically transmits to the transmitter a transmitter drive signal to cause the transmitter to transmit periodic ultrasonic signals. In one aspect of the present invention, each of the transmitter drive signals may be representative of substantially one cycle of a sinusoidal waveform.

The sensor drive circuit receives receiver output signals generated by the receiver responsive to the reception by the receiver of the ultrasonic signals generated by the transmitter. Each receiver output signal indicates the position of at least a portion of the web. The receiver output signals are then utilized to generate a sensor output signal indicative of the position of at least a portion of the web.

In one aspect of the present invention, the sensor drive circuit outputs receiver cutoff signals to selectively toggle the receiver in between a first mode wherein the receiver is permitted to form the receiver output signal responsive to the receiver sensing ultrasonic signals, and a second mode wherein the receiver is restricted from providing the receiver output signal.

The transmission of the periodic signals, and the selective toggling of the receiver cooperate to substantially eliminate the problems associated with the reflection of the sound waves in between the receiver, the transmitter or the web.

In one aspect, the present invention may include a temperature sensor for sensing the environmental temperature surrounding at least a portion of the sensor system and a microcontroller having access to a plurality of temperature compensation values. The microcontroller utilizes: (1) a temperature signal generated by the temperature sensor; (2) the receiver output signal; and (3) at least one of the temperature compensation values to generate a sensor output signal. In the sensor output signal, changes in the environmental temperature no longer have a substantial effect on the nature of the sensor output signal thereby improving the accuracy of the sensor system.

Other advantages and features will become apparent to those skilled in the art when the following description is read in conjunction with the attached drawings and the appended claims.

DETAILED DESCRIPTION OF THE INVENTION

Figure 1:
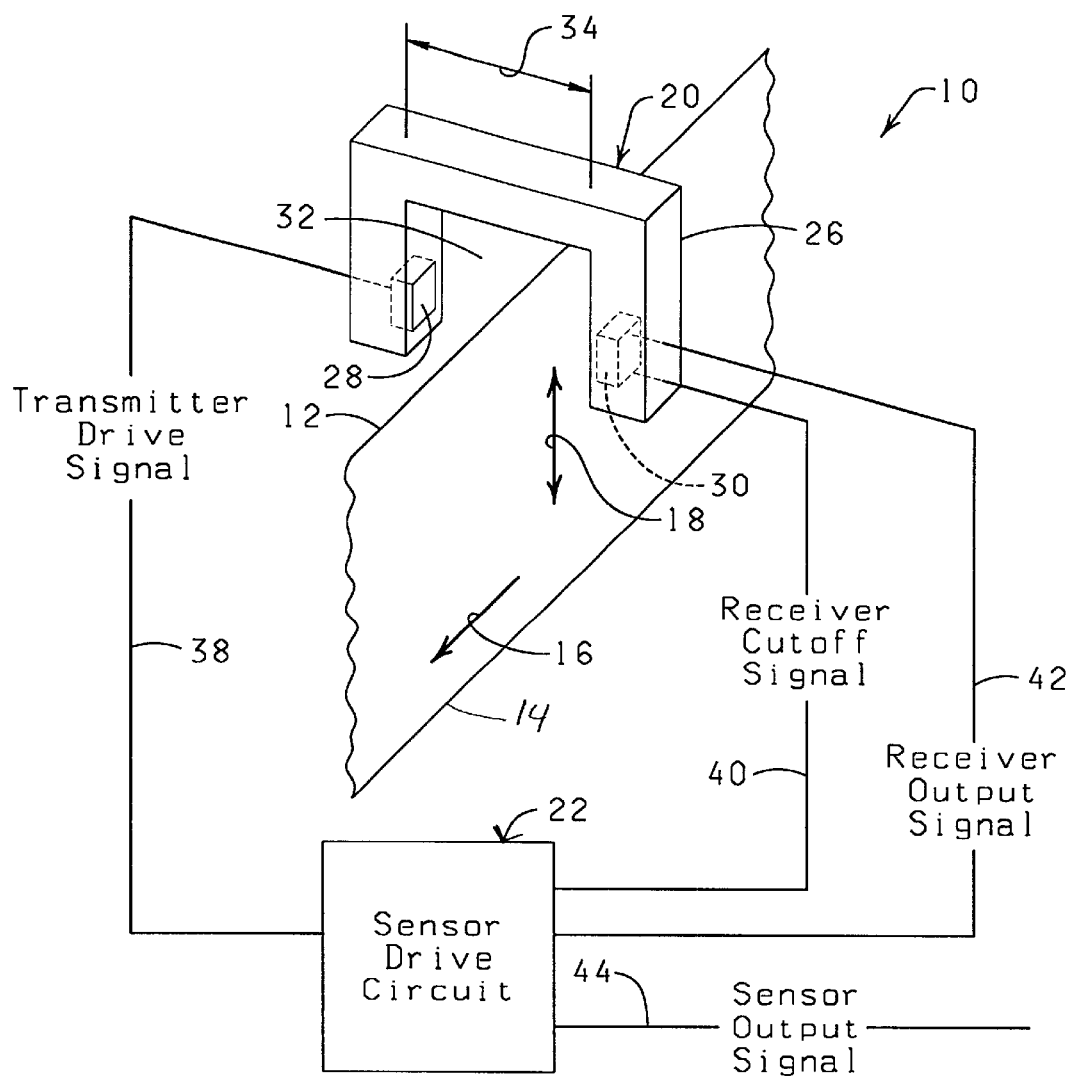
FIG. 1 is a schematic, diagrammatic view of one embodiment of an ultrasonic sensor system for web-guiding systems which is constructed in accordance with the present invention.

Referring now to the drawings and in particular to FIG. 1, shown therein is an ultrasonic sensor system 10 which is constructed in accordance with the present invention. The sensor system 10 is adapted and constructed to accurately determine the position of at least one edge 12 of a web of material 14, which may be a moving, continuous web of material and which is shown projecting out of the page. The web of material 14 can be either transparent or opaque, and may be moving in a web direction of travel 16, which is generally along the longitudinal axis of the web of material 14. As the web 14 moves along the web direction of travel 16, the web 14 may deviate in a direction 18, which is generally transverse to the web direction of travel 16.

The sensor system 10 includes a sensor apparatus 20 and a sensor drive circuit 22. The sensor apparatus 20 includes a housing 26, an ultrasonic transmitter 28, and an ultrasonic receiver 30. As shown in FIG. 1, the housing 26 supports the transmitter 28 and the receiver 30 on opposite sides of the web 14, and in use, the transmitter 28 and the receiver 30 are supported generally adjacent the edge 12 of the web 14. The housing 26 is preferably mounted perpendicularly with respect to the web direction of travel 16. The housing 26 serves to space the transmitter 28 from the receiver 30 to form a gap 32 therebetween. The gap 32 has a width 34 extending generally in between the transmitter 28 and the receiver 30.

Generally, the sensor drive circuit 22 periodically outputs: (1) a transmitter drive signal to the transmitter 28 via a signal path 38 to cause the transmitter 28 to generate an ultrasonic signal; and (2) a receiver cutoff signal to the receiver 30 via signal path 40 to permit the receiver 30 to receive at least a portion of the ultrasonic signal generated by the transmitter 28. In response thereto, the receiver 30 outputs a receiver output signal to the sensor drive circuit 22 via a signal path 42. The receiver output signal is indicative of the position of the edge 12 of the web of material 14. In response to receiving the receiver output signal, the sensor drive circuit 22 enhances the receiver output signal by taking into consideration environmental factors which can degrade accuracy, such as temperature. This is accomplished so as to generate a sensor output signal in which changes in the environment temperature no longer have a substantial effect on the nature of the sensor output signal. The sensor drive circuit 22 outputs the enhanced sensor output signal via a signal path 44 so that such sensor output signal can be received by a conventional web guiding microcontroller (not shown) to guide the web of material 14. The sensor output signal can be a voltage-to-current converted signal having a range of between 0 to 10 milliamperes.

The transmitter drive signal output by the sensor drive circuit 22 via the signal path 38 can be about one cycle of a substantially sinusoidal waveform having a frequency of about 150 kHz, for example. The receiver cutoff signal transmitted by the sensor drive circuit 22 can be selectively toggled between a first mode and a second mode. In the first mode, the receiver cutoff signal turns the receiver 30 "on" so as to permit the receiver 30 to form the receiver output signal responsive to the receiver 30 sensing ultrasonic signals. In the second mode, the receiver 30 is substantially turned "off" so that the receiver 30 cannot provide the receiver output signal responsive to the receiver 30 sensing ultrasonic signals. The receiver 30 can be turned "off" by the receiver cutoff signal in the second mode, by clamping the positive terminal of the receiver 30 to ground, for example.

In one embodiment, the receiver cutoff signal is continuously maintained in the second mode so as to turn the receiver 30 "off", and selectively toggled to the first mode to turn the receiver 30 "on" for a predetermined time coincident with the transmitting of the transmitter drive signal by the transmitter 28, so that the receiver 30 can generate the transmitter drive signal. After the predetermined time has passed, the sensor drive circuit 22 automatically toggles the receiver cutoff signal from the first mode to the second mode to turn the receiver 30 "off" to restrict the receiver 30 from generating any noise in the receiver output signal. Typically, the sensor drive circuit 22 transmits the transmitter drive signal to the transmitter 28, and about simultaneously toggles the receiver cutoff signal from the second mode to the first mode to turn the receiver 30 "on" for the predetermined time (to permit the receiver 30 to receive the ultrasonic signal generated by the transmitter 28 caused by the transmitter drive signal and to generate the receiver output signal in response thereto). The sensor drive circuit 22 then automatically switches the receiver cutoff signal from the first mode to the second mode to turn the receiver 30 "off" after the predetermined time has passed (to eliminate any noise in the receiver output signal caused by reflections of the ultrasonic signal generated by the transmitter 28). Thus, the receiver 30 is only permitted to generate the receiver output signal during each period for the predetermined time after the transmitter drive signal has been transmitted to the transmitter 28. The predetermined time that the receiver 30 is permitted to generate the receiver output signal is tuned for a period so as to permit the ultrasonic signal to be transmitted by the transmitter 28 across the gap 32 and thereby received by the receiver 30. The predetermined time that the receiver 30 is permitted to generate the receiver output signal is tuned for a period to also prevent any reflections of the ultrasonic signal being received by the receiver 30. Thus, it can be seen that the predetermined time will be determined by: (1) the frequency of the transmitter drive signal; and (2) the width 34 of the gap 32. Given a transmitter drive signal of about 150 kHz, and a width 34 of about one inch, a predetermined time period between about 100 microseconds to about 195 microseconds has been found to be appropriate, depending on the amount of time that passes between the start of the transmit signal and the start of the receiver on signal.

Figure 2:
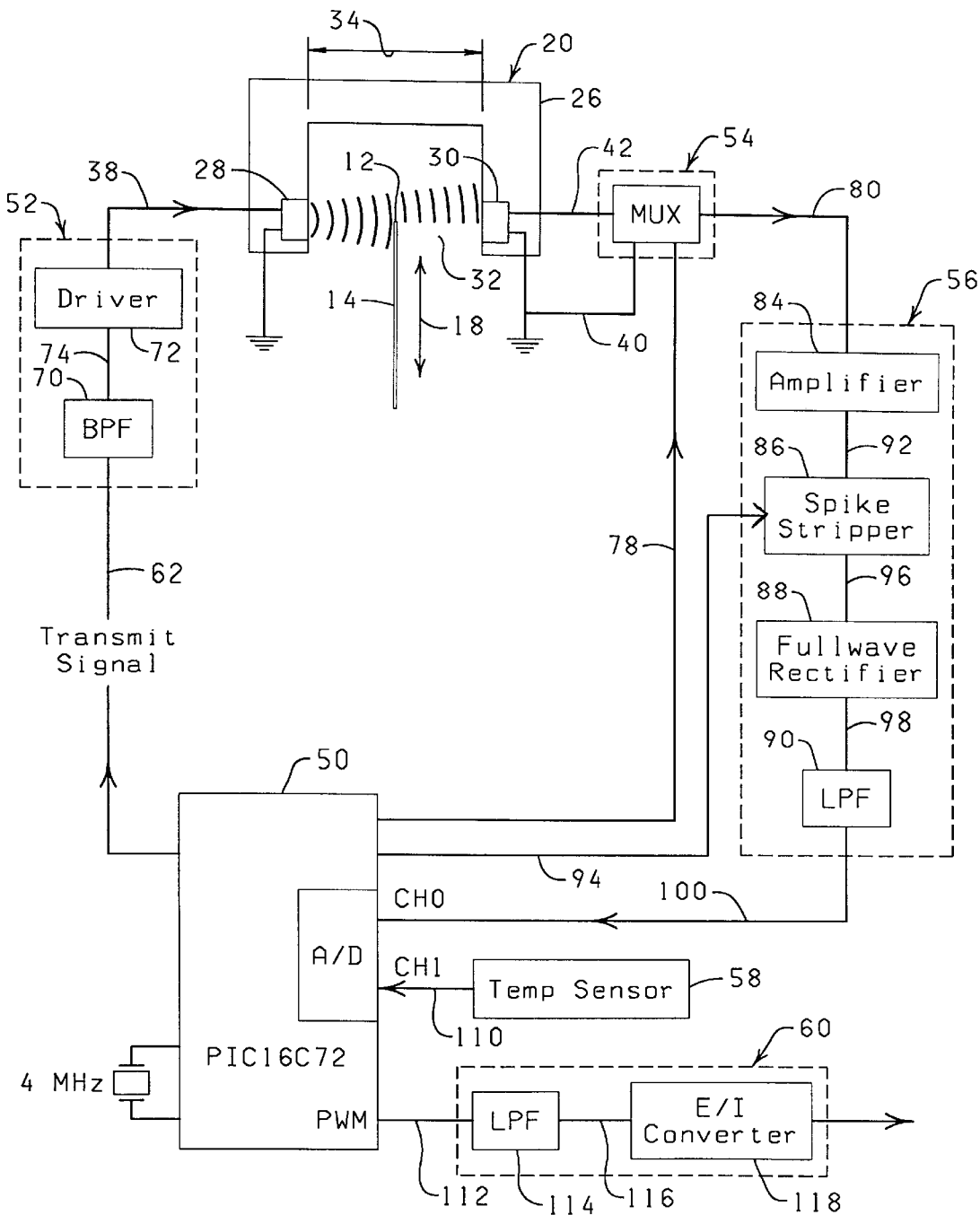
FIG. 2 is a schematic, diagrammatic view, in more detail, of the embodiment of the ultrasonic sensor system depicted in FIG. 1.

Referring now to FIG. 2, the sensor drive circuit 22 is shown in more detail. The sensor drive circuit 22 includes a microcontroller 50, a transmitter circuit 52, a receiver cutoff circuit 54, a signal conditioning circuit 56, a temperature sensor 58, and a sensor output converter circuit 60. In use, the microcontroller 50 periodically transmits a transmit signal to the transmitter circuit 52 via a signal path 62. The transmit signal can be representative of substantially one cycle of a substantially sinusoidally shaped waveform. The transmit signal can have a preselected frequency of about 150 kHz. The period at which the microcontroller 50 transmits the transmit signal can be about 5 milliseconds.

The transmitter circuit 52 receives the periodic transmit signals from the microcontroller 50, and, in response thereto, the transmitter circuit 52 conditions the transmit signal to drive the transmitter 28. In general, the transmitter circuit 52 is adapted and constructed to block all unwanted frequencies in the transmit signal, and to amplify the transmit signal so as to effectively drive the transmitter 28.

As shown in FIG. 2, the transmitter circuit 52 may include a band pass filter 70 and a driver 72. The band pass filter 70 is tuned to pass substantially only the selected frequency of the transmit signal and to block substantially all other frequencies, including harmonic frequencies and noise which may result from the transmission of the transmit signal, and a 60-Hz supply voltage, for example.

It will be understood by those skilled in the art that band pass filters, such as the band pass filter 70, may pass frequencies which are close to the selected frequency upon which the band pass filter is tuned. For this reason, the term "substantially only the selected frequency" as used herein is intended to encompass the selected frequency and any frequencies within the range of from about 140 kHz to about 160 kHz (when the selected frequency is about 150 kHz), or preferably within about 6.67 percent (±6.67%) of the selected frequency, although a greater range may be suitable in some applications. Of course, the range of frequencies encompassed by such term may also depend on many factors, such as the type of band pass filter, and the particular selected frequency.

The band pass filter 70 outputs the filtered transmit signal via a signal path 74 to be received by the driver 72. The driver 72 receives such filtered transmit signal and in response thereto, the driver 72 conditions the filtered transmit signal to effectively drive the transmitter 28.

The transmitter 28 receives the transmitter drive signal output by the driver 72, and in response thereto, the transmitter 28 outputs the ultrasonic signal (as indicated by the curved lines in FIG. 2). When the edge 12 of the web of material 14 is disposed in between the transmitter 28 and the receiver 30 (as shown in FIG. 2), the web of material 14 blocks a portion of the ultrasonic signal generated by the transmitter 28, as the ultrasonic signal travels across the gap 32. The unblocked portion of the ultrasonic signal generated by the transmitter 28 travels across the gap 32 and is received by the receiver 30. As will be understood by those skilled in the art, the amount of the ultrasonic signal which is blocked by the web 14 determines the indicated position of the edge 12.

As the edge 12 of the web of material 14 moves to block more of the path between the receiver 30 and the transmitter 28, the energy received by the receiver 30 decreases. As the edge 12 of the web of material 14 moves in the opposite direction to block less of the path, the energy received by the receiver 30 increases. This change in received energy produces an analog output signal indicative of the position of the edge 12 of the web of material 14.

To selectively switch the receiver 30 from the second mode to the first mode (to permit the receiver 30 to generate the receiver output signal), the microcontroller 50 transmits a signal to the receiver cutoff circuit 54 via a signal path 78. In response to receiving the signal from the microcontroller 50, the receiver cutoff circuit 54 switches the state of the receiver 30 from the second mode to the first mode to enable the receiver 30 to generate the receiver output signal. The microcontroller 50 outputs the respective signals to the transmitter circuit 52 and the receiver cutoff circuit 54, so that the receiver 30 will be enabled to generate the receiver output signal before the ultrasonic signal generated by the transmitter 28 travels across the gap 32 and is thereby received by the receiver 30.

After the receiver 30 has output the receiver output signal, the microcontroller 50 outputs a signal via the signal path 78 to the receiver cutoff circuit 54 to automatically switch the mode of the receiver 30 from the first mode to the second mode whereby the receiver 30 is turned "off" to prevent any noise in the receiver output signal caused by the reflections of the ultrasonic signal. As shown in FIG. 2, in one embodiment the receiver cutoff circuit 54 can be a multiplexer which selectively clamps the positive and negative terminals of the receiver 30 to ground.

The receiver output signal (which is typically an AC signal) is received by the receiver cutoff circuit 54. In response thereto, the receiver cutoff circuit 54 transmits the receiver output signal to the signal conditioning circuit 56 via a signal path 80. The signal conditioning circuit 56 includes an amplifier 84, a spike stripper 86, and a circuit for converting an AC signal into a DC signal, such as a full wave rectifier 88 and a low pass filter 90.

The amplifier 84 of the signal conditioning circuit 56 receives the receiver output signal from the receiver cutoff circuit 54. In response thereto, the amplifier 84 amplifies such receiver output signal. The amplified receiver output signal is then output to the spike stripper 86 via a signal path 92.

The spike stripper 86 receives the amplified receiver output signal via the signal path 92, and a signal from the microcontroller 50 via a signal path 94. In response thereto, the spike stripper 86 removes all voltage spikes from the amplified receiver output signal which may be caused by the switching of the receiver 30 from the first mode to the second mode, and from the second mode to the first mode.

The stripped, amplified receiver output signal is then output by the spike stripper 86 to the full wave rectifier 88 via a signal path 96. The spike stripper 86 can be a sample and hold amplifier circuit, which is known in the art.

The full wave rectifier 88 receives the signal output by the spike stripper 86, and in response thereto, the full wave rectifier 88 full wave rectifies such received signal. The rectified signal is then output by the full wave rectifier 88 to the low pass filter circuit 90 via a signal path 98. The low pass filter 90 serves to smooth the signal output by the full wave rectifier 88 to form a DC signal having a magnitude indicative of the position of the edge 12 of the web 14. The DC signal is output by the low pass filter circuit 90 to the microcontroller 50 via a signal path 100.

Because the transmitter 28, the receiver 30, and various other components of the sensor system 10 may be sensitive to changes in temperature, the sensor drive circuit 22 is adapted to correct the receiver output signal for changes in the environmental temperature surrounding the sensor system 10. This temperature correction provides for a more accurate representation of the position of the edge 12 of the web of material 14. The temperature sensor 58 generates a temperature signal indicative of the absolute temperature surrounding the sensor system 10. The temperature signal generated by the temperature sensor 58 is then output to the microcontroller 50 via a signal path 110. The microcontroller 50 receives the signal from the low pass filter circuit 90 and the temperature signal from the temperature sensor 58. In response thereto, the microcontroller 50 utilizes at least one of a plurality of stored temperature compensation values to generate a sensor output signal which more accurately describes the location of the edge 12 of the web of material 14.

The sensor output signal may be converted into any desirable format required by a particular web guide control system by the sensor output converter circuit 60. For example, the microcontroller 50 may be adapted to output the sensor output signal via a signal path 112 in a pulse width modulated format. The pulse width modulated sensor output signal is received by a low pass filter 114 of the sensor output converter circuit 60. The filtered signal is then output by the low pass filter circuit 114 via a signal path 116 to be received by a voltage-to-current converter 118. The voltage-to-current converter 118 converts the filtered pulse width modulated signal into a current sensor output signal which may have a magnitude ranging from between 0 to 10 milliamperes, if desired.

Figure 3:
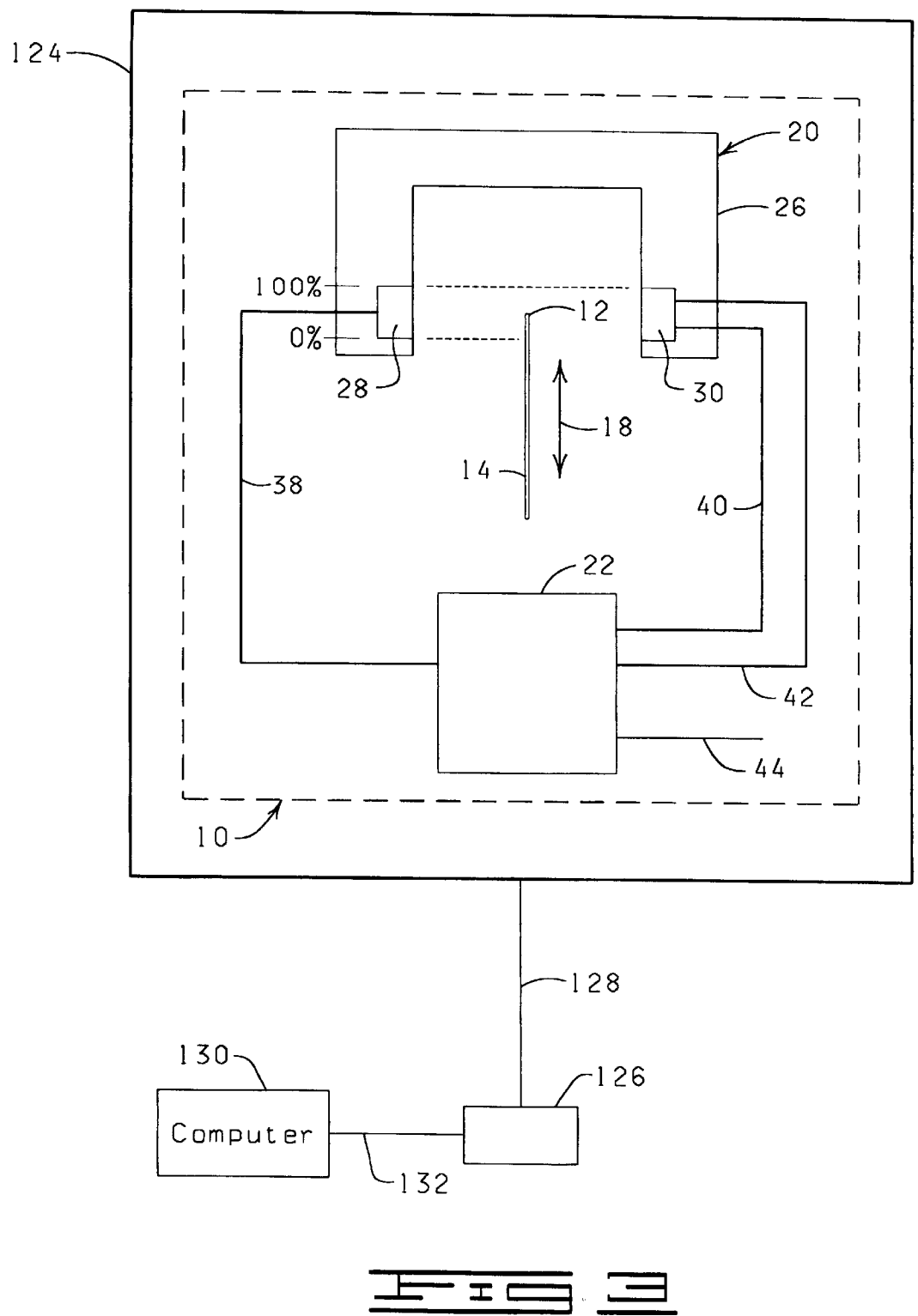
FIG. 3 is a schematic, diagrammatic view of a process for calibrating the sensor system to compensate for at least one environmental condition.

Referring now to FIG. 3, the sensor system 10 is calibrated for temperature after the sensor system 10 has been constructed, but before the sensor system 10 is utilized to guide the web 14 as follows. The sensor system 10 is disposed into an environmental chamber 124. The environmental chamber 124 can be a conventional environmental chamber. The microcontroller 50 is then connected to communicate with an interface device 126 via a signal path 128 so that the signal from the low pass filter 90, and the temperature signal from the temperature sensor 58 are output by the microcontroller 50 to the interface device 126. When the microcontroller 50 is a Model PIC16C72 microprocessor, the signal path 128 can be an ICbus which is connected to the "SCL" and "SDA" outputs on such microprocessor.

The interface device 126 receives the signals transmitted by the microcontroller 50, and converts such signals into signals capable of being received by a computer 130 via a signal path 132. The computer 130 can be a standard personal computer, and the signal path 132 can be an RS232 serial bus. Thus, it can be seen that the signal from the low pass filter 90, and the temperature signal from the temperature sensor 58 are communicated by the microcontroller 50 to the computer 130 via the interface device 126, and the signal paths 128 and 132, so that the computer 130 receives the signals which are indicative of the position of the web 14, and the temperature in real time.

The microcontroller 50 is operated so as to output the transmit signal and the receiver cutoff signal, as described previously. In this regard, the transmitter 28 outputs the periodic, ultrasonic signals to be received by the receiver 30 when the receiver 30 is disposed in the first mode and is thereby enabled to generate the receiver output signal, as discussed above. The receiver output signal is then passed through the receiver cutoff circuit 54 and the signal conditioning circuit 56. Thus, periodic signals indicative of the location of the web 14 are being received by the microcontroller 50 on the signal path 100. Simultaneously, the temperature sensor 58 is transmitting temperature signals indicative of the absolute temperature of the environment in which the sensor system 10 is disposed to the microcontroller 50 on the signal path 110.

While the sensor system 10 is operating during calibration, as discussed previously, the environmental temperature surrounding the sensor system 10 is swept through a range from about 32° F. to about 140° F. The microcontroller 50 receives the signal indicative of the location of the web 14 on the signal path 100, and the temperature signal on the signal path 110. These two signals, which may both be analog signals, are converted by the microcontroller 50 into digital signals, if necessary. The two signals are then transmitted to the computer 130 via the interface device 126 and signal paths 128 and 132, as previously discussed.

The computer 130 is provided with an algorithm which computes an array of the temperature compensation values based on the signal indicative of the location of the web 14, and the temperature signal. It should be noted that during calibration, the edge 12 of the web 14 is maintained in a fixed, known location between the transmitter 28 and the receiver 30.

At each temperature within the temperature range discussed above, one of the temperature compensation values is computed by the computer 130. In this regard, the computer 130 utilizes the following formula to determine each temperature compensation value:

$$\text{Comp. Value} \bigg|_{@t° F.} = \left| \frac{X}{\text{Measured Value}} \bigg|_{@t° F.} \right| \quad 32° \le t \le 140° F.$$

where: X=the non-temperature dependent value for a fixed web position; and the Measured Value at t° F. the magnitude of the signal indicative of the location of the web 14 received by the microcontroller 50 on the signal path 100.

Each of the temperature compensation values computed by the computer 130 utilized in the above formula is stored on the computer 130 in the form of a table including individual temperatures and the corresponding temperature compensation value for each temperature.

After the temperature has been swept in the environmental chamber 124 and the computer 130 has calculated each of the temperature compensation values, the microcontroller 50 is programmed with the table produced by the computer 130 so that the microcontroller 50 has access to such table.

The table of information programmed (or stored) in the microcontroller 50 is then utilized by the microcontroller 50 to generate the sensor output signal so that changes in the environmental temperature no longer have a substantial effect on the nature of the sensor output signal generated by the microcontroller 50. That is, the microcontroller 50 reads the temperature signal produced by the temperature sensor 58 to determine the temperature at which the sensor system 10 is currently operating. Then, the microcontroller 50 utilizes the temperature sensor to look up in the table the temperature compensation value corresponding to the temperature signal output by the temperature sensor 58.

The microcontroller 50 also receives the signal indicative of the location of the web 14 on the signal path 100 and converts the same into a digital signal. The digital signal indicative of the location of the web 14 is then multipled by the previously located temperature compensation value to produce the sensor output signal.

Changes may be made in the embodiments of the invention described herein, or in the parts or the elements of the embodiments described herein, or in the steps or sequence of steps of the methods described herein, without departing from the spirit and/or the scope of the invention as defined in the following claims.

What is claimed is:

1. A sensor system for determining the position of at least one edge of a web of material, the sensor system comprising:
   a transmitter being capable of selectively transmitting ultrasonic signals;
   a receiver positioned to receive at least a portion of the ultrasonic signals transmitted by the transmitter and being capable of generating receiver output signals indicative of the position of the web;
   means for periodically transmitting to the transmitter a transmitter drive signal with each transmitter drive signal representative of substantially one cycle of a substantially sinusoidal waveform having a selected frequency; and
   means for receiving receiver output signals from the receiver with each receiver output signal being indicative of the position of at least a portion of the web.

2. A sensor system as defined in claim 1, further comprising means for generating sensor output signals responsive to the receiving of the receiver output signals.

3. A sensor system as defined in claim 1, further comprising means for sensing an environmental temperature surrounding at least a portion of the sensor system, and for enhancing the receiver output signals with at least one stored temperature compensation value so as to generate a sensor output signal in which changes in the environmental temperature no longer have a substantial effect on the nature of the sensor output signal.

4. A sensor system as defined in claim 1, wherein the means for periodically transmitting further comprises means for selectively toggling the receiver in between a first mode wherein the receiver is permitted to form the receiver output signals responsive to the receiver sensing ultrasonic signals, and a second mode wherein the receiver is restricted from providing the receiver output signals.

5. A sensor system as defined in claim 4, wherein the receiver is toggled from the second mode to the first mode to permit the receiver to receive the ultrasonic signals generated by the transmitter, and then the receiver is automatically toggled back to the first mode after a predetermined time so as to eliminate any noise in the receiver output signals caused by reflections of the ultrasonic signals.

6. A sensor system as defined in claim 1, further comprising:
    means for receiving the transmitter drive signal and for blocking substantially all frequencies except for the selected frequency so that substantially only the selected frequency is transmitted to the transmitter.

7. A sensor system as defined in claim 1, further comprising:
    means for receiving the receiver output signals and for converting the receiver output signals into a DC signal having a magnitude indicative of the position of the web.

8. A sensor system as defined in claim 7, further comprising: means for converting the DC signal into a digital signal.

9. The sensor system of claim 3, wherein the stored temperature compensation values are multiplied with the receiver output signals.

10. The sensor system of claim 4, wherein the receiver is toggled to the second mode by clamping the receiver to ground.

11. The sensor system of claim 5, wherein the stored temperature compensation values are multiplied with the receiver output signals.

12. A sensor system for determining the position of at least one edge of a web of material, the sensor system comprising:
    a transmitter being capable of selectively transmitting an ultrasonic signal;
    a receiver positioned to receive at least a portion of the ultrasonic signal transmitted by the transmitter and being capable of generating an output signal indicative of the position of the web;
    means for periodically transmitting to the transmitter a transmitter drive signal so as to cause the transmitter to transmit the ultrasonic signal; and
    means for toggling the receiver in between a first mode wherein the receiver is permitted to form a receiver output signal responsive to the receiver sensing the ultrasonic signal, and a second mode wherein the receiver is restricted from providing the receiver output signal, the receiver output signal being indicative of the position of at least a portion of the web.

13. A sensor system as defined in claim 12, further comprising means for generating a sensor output signal responsive to the receiving of the receiver output signal.

14. A sensor system as defined in claim 12, further comprising means for sensing an environmental temperature surrounding at least a portion of the sensor system, and for enhancing the receiver output signal with at least one stored temperature compensation value so as to generate a sensor output signal in which changes in the environmental temperature no longer have a substantial effect on the nature of the sensor output signal.

15. A sensor system as defined in claim 12, wherein the receiver is toggled from the second mode to the first mode about simultaneously with the transmission of the transmitter drive signal to permit the receiver to receive the ultrasonic signal generated by the transmitter, and thereafter the receiver automatically being toggled back to the first mode after a predetermined time so as to eliminate any noise in the receiver output signal caused by reflections of the ultrasonic signal.

16. A sensor system as defined in claim 12, wherein the transmitter drive signal has a selected frequency, and wherein the sensor system further comprises:
    means for receiving the transmitter drive signal and for blocking substantially all frequencies except for the selected frequency so that substantially only the selected frequency is transmitted to the transmitter.

17. A sensor system as defined in claim 12, further comprising:
    means for receiving the receiver output signal and for converting the receiver output signal into a DC signal having a magnitude indicative of the position of the web.

18. A sensor system as defined in claim 17, further comprising:
    means for converting the DC signal into a digital signal.

19. The sensor system of claim 12, wherein the receiver is toggled to the second mode by clamping the receiver to ground.

20. The sensor system of claim 14, wherein the stored temperature compensation values are multiplied with the receiver output signals.

21. The sensor system of claim 15, wherein the receiver is toggled to the second mode by clamping the receiver to ground.

22. A sensor system for determining the position of at least one edge of a web of material, the sensor system comprising:
    a transmitter being capable of selectively transmitting ultrasonic signals;
    a receiver positioned to receive at least a portion of the ultrasonic signals transmitted by the transmitter and being capable of generating receiver output signals indicative of the position of the web;
    means for periodically transmitting to the transmitter a transmitter drive signal;
    means for receiving receiver output signals from the receiver with each receiver output signal being indicative of the position of at least a portion of the web; and
    means for sensing an environmental temperature surrounding at least a portion of the sensor system, and for enhancing the receiver output signal with at least one stored temperature compensation value so as to generate a sensor output signal in which changes in the environmental temperature no longer have a substantial effect on the nature of the sensor output signal.

23. A sensor system as defined in claim 22, further comprising means for generating a sensor output signal responsive to the receiving of the receiver output signals.

24. A sensor system as defined in claim 22, wherein the means for periodically transmitting to the transmitter the transmitter drive signal further comprises means for selectively toggling the receiver in between a first mode wherein the receiver is permitted to generate the receiver output signals responsive to the receiver sensing ultrasonic signals, and a second mode wherein the receiver is restricted from generating the receiver output signals.

25. A sensor system as defined in claim 24, wherein the receiver is toggled from the second mode to the first mode about simultaneously with the transmission of the transmitter drive signal to permit the receiver to receive the ultrasonic signals generated by the transmitter, and then the receiver automatically being toggled back to the first mode after a predetermined time so as to eliminate any noise in the receiver output signals caused by reflections of the ultrasonic signals.

26. A sensor system as defined in claim 22, wherein the transmitter drive signal has a selected frequency, and wherein the sensor system further comprises:

means for receiving the transmitter drive signal and for blocking substantially all frequencies except for the selected frequency so that substantially only the selected frequency is transmitted to the transmitter.

27. A sensor system as defined in claim 24, further comprising:

means for receiving the receiver output signals and for converting the receiver output signals into a DC signal having a magnitude indicative of the position of the web.

28. A sensor system as defined in claim 27, further comprising:

means for converting the DC signal into a digital signal.

29. The sensor system of claim 22, wherein the stored temperature compensation values are multiplied with the receiver output signals.

30. The sensor system of claim 24, wherein the receiver is toggled to the second mode by clamping the receiver to ground.

31. The sensor system of claim 25, wherein the receiver is toggled to the second mode by clamping the receiver to ground.

* * * * *